(12) United States Patent
Haeggström et al.

(10) Patent No.: US 10,098,842 B2
(45) Date of Patent: Oct. 16, 2018

(54) METHOD AND A DEVICE FOR PRODUCING NANOPARTICLES

(71) Applicant: Nanoform Finland Oy, Helsinki (FI)

(72) Inventors: Edward Haeggström, Helsinki (FI); Jouko Yliruusi, Vantaa (FI); Kai Falck, Helsinki (FI); Heikki Räikkönen, Helsinki (FI); Jenni Pessi, Helsinki (FI); Ilkka Lassila, Helsinki (FI); Antti Meriläinen, Helsinki (FI)

(73) Assignee: Nanoform Finland Oy, Helsinki (FI)

(*) Notice: Subject to any disclaimer, the term of this patent is extended or adjusted under 35 U.S.C. 154(b) by 0 days.

(21) Appl. No.: 15/512,070

(22) PCT Filed: Oct. 5, 2015

(86) PCT No.: PCT/FI2015/050664
§ 371 (c)(1),
(2) Date: Mar. 17, 2017

(87) PCT Pub. No.: WO2016/055696
PCT Pub. Date: Apr. 14, 2016

(65) Prior Publication Data
US 2017/0231914 A1   Aug. 17, 2017

(30) Foreign Application Priority Data

Oct. 6, 2014 (FI) ..................... 20140266

(51) Int. Cl.
*B01J 3/00* (2006.01)
*A61K 9/14* (2006.01)
*A61K 31/5415* (2006.01)

(52) U.S. Cl.
CPC ............ *A61K 9/14* (2013.01); *A61K 31/5415* (2013.01); *B01J 3/008* (2013.01); *Y02P 20/544* (2015.11)

(58) Field of Classification Search
CPC ...................................................... B01J 3/008
See application file for complete search history.

(56) References Cited

U.S. PATENT DOCUMENTS

2006/0153921 A1   7/2006   Chattopadhyay
2007/0284769 A1   12/2007  Kato

FOREIGN PATENT DOCUMENTS

WO   WO9714407   4/1997
WO   WO9731691   9/1997
(Continued)

OTHER PUBLICATIONS

Chingunpitak et al, "Micronization of Dihydroartemeinin by Expansion of Supercritical Solutions", Drug Development and Pharmacy, vol. 22, No. 6, Jun. 1, 1987.*
(Continued)

*Primary Examiner* — Carlos A Azpuru
(74) *Attorney, Agent, or Firm* — BelayIP Oy (57) ABSTRACT

The invention relates to a method and a device for producing nanoparticles of organic substances, in particular by controlled expansion of pressurized solutions. The method comprises: admixing the organic substance and a supercritical fluid to form a mixture at a first pressure; decreasing the first pressure gradually to a second pressure so that a flow of the mixture is formed and nucleation of the organic substance in the mixture is initiated; and, decreasing the second pressure to a third pressure, so that solidification of the fluid of the mixture, comprising the nucleated organic substance, is initiated. The device comprises: a pressure chamber (1) for a mixture of the organic substance and a supercritical fluid; a collection chamber (5) for the nanoparticles; an outlet tube (2) connecting the pressure chamber to the collection chamber (5); and, one or more second nozzles (6). The outlet tube is provided with a pressure controlling means (3) configured to control pressure of the mixture (Continued)

within the outlet tube and a first nozzle (4) configured to allow expansion of the mixture to the collection chamber.

13 Claims, 7 Drawing Sheets

(56) References Cited

FOREIGN PATENT DOCUMENTS

| WO | 9858722 A1 | * | 12/1998 |
| WO | WO9858722 | | 12/1998 |
| WO | WO9965469 | | 12/1999 |
| WO | WO2006015358 | | 2/2006 |
| WO | 2007072072 | | 6/2007 |
| WO | 2007072072 A2 | * | 6/2007 |

OTHER PUBLICATIONS

Chingunpitak et al, "Micronization of Dihydroartemisinin by Rapid Expansion of Super Critical Fluids", Drug development and Industrial Pharmacy, vol. 34, No. 6, 2008, pp. 609-617.*

Chingunpitak J et al., "Micronization of Dihydroartemisinin by rapid expansion of supercritical solutions"; Drug Development and Industrial Pharmacy, Jun. 1, 2008 New York, NY, US CPC: Source information: vol. 34, No. 6, 2008 pp. 609-617.

Zhang F X, Wei X L, "The influences of the structure of nozzle on coating effect in particle coating by fluid-rapid expansion of supercritical solutions"; Advanced Materials Research, Dec. 1, 2013 Trans Tech Publications Ltd, CH, vol. 864-867,pp. 1204-1207; Dec. 13, 2013.

Matson D W, Petersen R C, Smith R D, "Production of powders and films by the rapid expansion of supercritical solutions"; Journal of Materials Science, Jun. 1, 1987 Kluwer Academic Publishers, Dordrecht; vol. 22, No. 6, pp. 1919-1928; Jun. 1987.

Zen Wen et al. "Application of an improved RESS process for atractylodes macrocephala koidz colatile oil liposomes production" in the proceedings of the 4th international conference on bioinformatics and biomedical engineering (iCBBE) Jun. 2010.

Ikeda et al. "Enganced skin permeation of piroxicam and pranoprofen induced from nanoparticles dispersed in propylene glycol aqueous solution", EMBASE/Elsevier abstract 2012.

Hezave et al. "The effects of RESS parameters on the diclofenac particle size" in Advanced power technology, vol. 22, Iss. 5, Sep. 2011.

Kayrak et al. "Micronization of Ibuprofen by RESS" in The Journal of Supercritical Fluids, vol. 26, Iss. 1, May 2003.

* cited by examiner

METHOD AND A DEVICE FOR PRODUCING NANOPARTICLES

FIELD

The invention relates to a method and a device for producing nanoparticles of organic substances, in particular by controlled expansion of pressurized solutions.

BACKGROUND

Nanoparticles exhibit size-dependent physical and chemical properties, such as reduced melting point and increased reactivity and solubility. These special properties of nanoparticles are often due to their large surface area. The increase in solubility of nanosized material is a thermodynamic effect that results from the increased chemical potential at a curved surface.

In a typical RESS (rapid expansion of supercritical solutions) process, supercritical fluid is used to dissolve solid material under high pressure and temperature, thus forming a homogeneous supercritical phase. Thereafter, the solution is expanded through a nozzle, and small particles are formed. At the rapid expansion point right at the opening of the nozzle, there is a sudden pressure drop that forces the dissolved material to precipitate out of the solution. The crystals that are instantly formed enclose a small amount of the solvent that, due to the expansion, changes from supercritical fluid to its normal state, thus breaking the crystal from inside-out. The particles that are formed this way may have a diameter of a few hundreds of nanometers.

Supercritical fluid processing techniques have shown promise in production of small particles of water-insoluble materials. For example WO 97/14407 and WO 99/65469 describe processes that generate submicron-size particles of biologically useful materials through the use of supercritical or compressed fluid processing techniques. However, these processes produce particle suspensions containing a substantial fraction of drug particles larger than 100 nm. Substantially smaller particles would be advantageous for medical applications. The process was further developed in WO 2006/015358 that discloses a method to prepare homogenous aqueous suspensions of nanoscale drug particles with the aid of stabilizing agents. According to the process disclosed in WO 2006/015358, all the formed particles are smaller than 100 nm, and standard deviation of particle size was less than 15 nm.

WO 97/31691 discloses a method and apparatus for particle precipitation and coating, wherein the precipitable substance is in contact with a supercritical antisolvent together with an energizing gas stream to generate focused high frequency sonic waves in the antisolvent to break the particles into smaller ones. The size or the particles obtained using the technology was 0.1-10 μm.

U.S. Pat. No. 7,815,426 discloses an apparatus and method for preparing nanoparticles wherein a suspension of an organic substance is passed through a micro flow channel, and the organic substance is irradiated with a laser beam.

US 2006/0153921 disclosed a method of producing particles from solution-in-supercritical fluid or compressed gas emulsions. According to this disclosure, a solution including a solute dissolved in a solvent is contacted with supercritical fluid or compressed gas to for a solution-in supercritical fluid or compressed gas emulsion. The emulsion is sprayed through an orifice to create spray droplets from which the supercritical fluid or compressed gas is removed resulting in the formation of particles that include the solute. Finally, the solvent is removed e.g. by evaporation.

Figure 1:
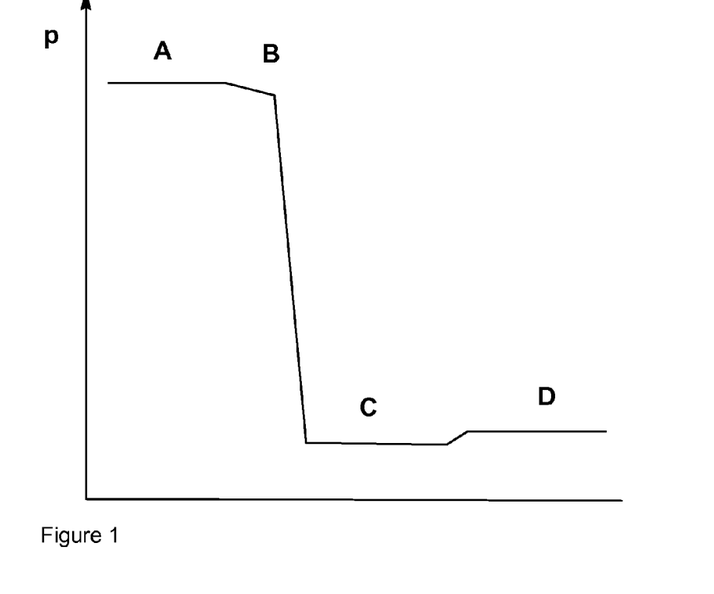
FIG. 1 shows a typical pressure profile of an RESS device.

A typical RESS is a two-step process. The first step is an extraction or solvation in which a supercritical fluid is saturated with the substrates of interest. This extraction is followed by a sudden depressurization through [PJJ1] a nozzle which produces a large decrease in the solvent power and the temperature of the fluid, therefore causing the precipitation of the solute. Key parameters of RESS process are the pre-expansion pressure and temperature, the expansion pressure, and the nozzle design. An approximate pressure profile in a RESS process is shown in FIG. 1. As the ratio between the pre-expansion pressure (A) and the expansion pressure (C) are typically very high, sonic velocities are achieved at the outlet of the nozzle, and a supersonic jet that ends at the Mach disc is formed. Most of the pressure drop is produced at a supersonic free jet (C). The pressure in this region can be below the bulk pressure of the expansion vessel (D). This depressurization also causes drastic decrease in temperature, which can lead to $CO_2$ condensation or freezing. At the end of supersonic region a Mach shock is formed and the pressure is increases up to the ambient pressure, accompanied by an increase in temperature.

Since in a RESS process $scCO_2$ is expanded through the capillary nozzle, first possible pressure reduction (B) takes place in the capillaries of the nozzle. Nucleation may start in the nozzle capillaries, due to small pressure reduction. The greater pressure reduction takes place as the fluid such as $CO_2$ enters the collection chamber and thus most of the nucleation takes place there.

Accordingly, in a RESS process nucleation takes mainly place after the exit nozzle. Due to the sudden pressure drop from the pre-expansion pressure to the post-expansion pressure, the supersaturation level is high and number of nuclei formed is large and the size of these nuclei small. The nuclei are grown mainly by coagulation in the collection chamber. Coagulation is caused by the high flow velocities and the density differences, caused by Mach disk formation, in the collection chamber.

Since nanoparticles find many potential applications and, since there is a limited number of processes to produce them, there is a need to develop new methods to prepare such particles.

SUMMARY

The present invention is based on the observation that less than 20 nm nanoparticles can be obtained, in contrast to the RESS process of prior art, by using a gradient pressure reduction process that creates conditions for controlled expansion of supercritical solutions.

According to one aspect the present invention concerns a new method for producing nanoparticles of an organic substance, the method including:
  admixing the organic substance and a supercritical fluid to form a mixture at a first pressure,
  decreasing the first pressure gradually to a second pressure in such a manner that a flow of the mixture is formed and nucleation of the organic substance in the mixture is initiated and
  decreasing the second pressure to a third pressure in such a manner that solidification of the fluid of the mixture, comprising the nucleated organic substance, is initiated.

According to another aspect, the present invention concerns a new device for producing nanoparticles of an organic substance, the apparatus including:
- a pressure chamber for a mixture of the organic substance and a supercritical fluid,
- a collection chamber for the nanoparticles of the organic substance,
- an outlet tube connecting the pressure chamber to a collection chamber, the outlet tube being provided with
- a pressure controlling means configured to control pressure of the mixture within the outlet tube, and
- a first nozzle configured to allow expansion of the mixture to the collection chamber,
- wherein the device further includes one or more second nozzles, for one or more second fluids, the one or more second nozzles being configured to allow adiabatic solidification of the one or more second fluids, and to allow subjecting the mixture expanding from the first nozzle to the solidifying one or more second fluids.

According to another aspect the present invention concerns use of the device of the present invention for producing nanoparticles of medicaments.

Further aspects of the present technology are described in the accompanying dependent claims.

Exemplifying and non-limiting embodiments of the invention, both as to constructions and to methods of operation, together with additional objects and advantages thereof, are best understood from the following description of specific exemplifying embodiments when read in connection with the accompanying drawings.

The verbs "to comprise" and "to include" are used in this document as open limitations that neither exclude nor require the existence of un-recited features. The features recited in the accompanied depending claims are mutually freely combinable unless otherwise explicitly stated. Furthermore, it is to be understood that the use of "a" or "an", i.e. a singular form, throughout this document does not exclude a plurality.

DESCRIPTION

Figure 2:
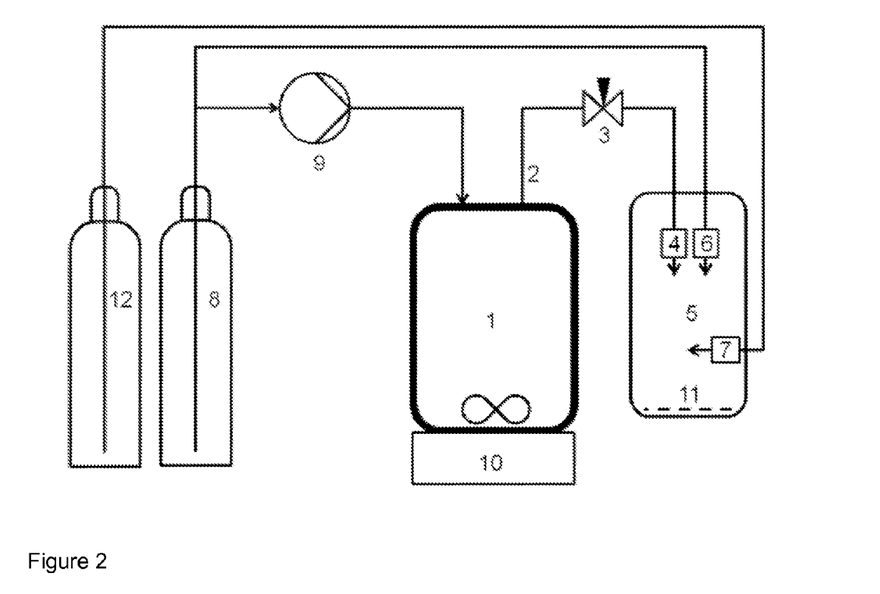
FIG. 2 shows a schematic illustration of a device for the preparation of nanoparticles according to an exemplary, non-limiting embodiment of the invention.

The present invention for producing nanoparticles of organic substances, preferably with narrow size distribution, is based on a pressure reduction process that creates conditions for controlled expansion of supercritical solutions (CESS). The process combines controlled flow, controlled pressure reduction, and preferably also particle collection. The pressure gradient process can also be generated by using a tapered tube with increasing cross section towards the orifice, and/or multiple nozzles, orifices or valves. An exemplary device suitable for the preparation of nanoparticles according to the present invention is shown in FIG. 2. In the following, the exemplary device shown in FIG. 2 is used to describe the method of the present invention.

According to one embodiment of the present invention, a mixture of the organic substance in a supercritical fluid is allowed to expand from a pressure chamber (1) to an outlet tube (2) equipped with pressure controlling means (3) and the first nozzle (4). The first pressure reduction step takes place in the outlet tube (2) connecting the pressure chamber (1) to the collection chamber (5). A pressure controlling means, for instance a needle valve, releases the substance solution through a first nozzle (4) to the collection chamber. The flow rate inside the outlet tube is kept low to ensure a controlled, preferably laminar or substantially laminar flow of the mixture. The pressure is allowed to decrease gradually inside the outlet tube causing supersaturation of the substance in the fluid, which initiates the nucleation process. Having the pressure reduction controlled and gradual, keeps the nucleate formation process slow which is important in order to prevent concentration of nuclei and blocking of the outlet tube. This slow nucleate formation together with the controlled laminar flow or at least substantially laminar flow in the outlet tube inhibits unwanted growth of the formed nuclei. However, the flow can also at least partially turbulent. Turbulence may occur especially in valves.

Figure 3:
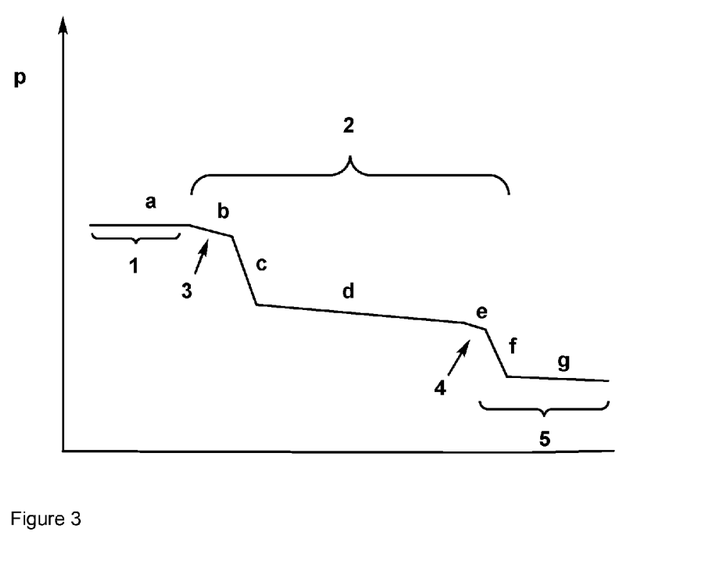
FIG. 3 shows an exemplary pressure profile of a device according to the present invention.

An exemplary pressure profile of a method of the present invention is shown in FIG. 3 obtainable by using the device shown in FIG. 2. Accordingly, the supercritical fluid comprising the substance is expanded in the outlet tube (2). The first pressure reduction takes place by using a pressure controlling means (3). According to the method, the pressure is decreased from the first pressure to the second pressure in the outlet tube connecting the pressure chamber and the collection chamber. As shown in the FIG. 3, the pressure in the outlet tube before the valve (3) is substantially equal to the pressure in the pressure chamber (1), and is then reduced gradually until the nozzle (4). The closer the valve is to the collection chamber (1), the longer is the part of the outlet tube where the pressure decrease is gradual. Since pressure is allowed to decrease gradually, supersaturation of the substance in the fluid occurs which initiates the nucleation.

As shown in FIG. 3, there is a small pressure reduction step (b) in the pressure controlling means. The second pressure reduction (c) takes place as the mixture is transported from the pressure controlling means to the outlet tube. The latter pressure reduction is controlled so that sonic velocities and Mach disk formation is prevented. There is also small gradual pressure reduction (d) in the outlet tube between the pressure controlling means and the first nozzle 4. The next pressure reduction (e) takes place in the nozzle capillary. The term gradual decrease from the first pressure to the second pressure should be understood as the overall pressure decrease in the outlet tube. When referring to FIG. 3, the gradual decrease includes the pressure drop prior to the exit of the first nozzle (i.e. (a)-(e)). Gradual pressure decrease prior to exit nozzle is essential, since it permits particle formation and growth in the outlet tube of the device. The final pressure reduction takes place when the mixture expands from the first nozzle to the collection chamber (5) (i.e. (e)→(f)→(g)). Velocities are controlled by the ratio of the pressure drop and by the restricted expansion space.

According to another embodiment, the method includes the gradual pressure drop from the first pressure to the second pressure by using an outlet tube including two or more pressure controlling means for achieving the desired pressure profile. The last pressure reduction, i.e. the decrease from the second pressure to the third pressure occurs when the mixture flows through the first nozzle to the collection chamber. The pressure reduction in the outlet tube can be done also by using plurality of pressure controlling means.

Decreasing the second pressure to a third pressure is done in such a manner that solidification of the fluid of the mixture, comprising the nucleated organic substance, is initiated. According to a preferable embodiment the solidification is adiabatic.

Pressure ranges in the method of the present invention are dependent on the solubility of the organic substance and the fluid used. Exemplary pressure range for supercritical carbon dioxide is 74-600 bar. Exemplary first pressures are 200-450 bar, and typical third pressures (i.e. back pressure in the collection chamber) are 1-4 bar. Exemplary pressure ranges suitable for preparation of piroxicam nanoparticles are collected in Table 1.

TABLE 1

| Exemplary pressure ranges | | |
|---|---|---|
| First pressure[a] | Second pressure[b] | Third pressure[c] |
| 200 bar | 20-22 bar | 3 bar |
| 333 bar | 33-38 bar | 4 bar |
| 400 bar | 40-46 bar | 4 bar |

[a]pressure in the pressure chamber;
[b]the first pressure decreased gradually to this pressure within the outlet tube,
[c]back pressure in the collection chamber.

Exemplary temperatures are 40-60° C. in the pressure chamber and 30-55° C. in the outlet tube.

According to an exemplary embodiment, temperature range in the system is from 31° C. to approximately 10° C. below the melting point of the substance. With certain substances also temperatures above the melting point can be used. Temperature, as the pressure, can be used to adjust the density of the fluid phase and solubility of the substance.

Near supercritical conditions can be used with organic substances with high solubility to supercritical fluid.

Pressure and temperature may be used to adjust the properties of the supercritical phase. These properties such as density and solvent power can be used to control the solubility of the solute in the supercritical phase, and thus also the supersaturation of the solute. However, temperature and pressure should not be considered to be absolute parameters for certain conditions, since same solvent power can be obtained by several temperature and pressure values resulting in the same density. Density of the phase affects also the flow rate.

According to an embodiment liquid $CO_2$ is transferred from a container (8) to a pressure chamber (1) using a high pressure pump (9). According to an exemplary embodiment $CO_2$ is pumped to the pressure required to form supercritical fluid (>74 bar) and temperature (>300 K). The substance, such as a drug molecule is introduced to the pressure chamber followed by admixing with the supercritical $CO_2$ ($scCO_2$) to form a supercritical fluid. Proper mixing and thus formation of a homogenous mixture can be ensured by using e.g. a magnetic mixer (10). The system pressure can be monitored with an internal pressure gauge of the pressure pump whereas the temperature can be monitored with a thermocouple and/or a thermometer. The pressure chamber is preferably equipped with temperature controlling means and pressure controlling means and is coated with an insulating material. The device is equipped with a collection chamber (5) which preferably is insulated. The pressure in the collection chamber is below the pressure in the pressure chamber when the device is operated.

An exemplary device used for preparation of nanoparticles of piroxicam included an outlet tube (2) of length and internal diameter of the outlet tube 60 cm, and 2 mm, respectively. The first pressure reduction takes place in the outlet tube in the aid of the needle valve (3). An exemplary flow rate was 24 mL/min. It is obvious for a skilled person that the flow rate and the decrease of the pressure required for nucleation initiation within the outlet tube depends on the nature of the organic substance and supercritical fluid used, temperature, as well as the construction of the device.

The second pressure reduction step takes place at the first nozzle (4). As the volume of the supercritical fluid such as $scCO_2$ increases, the pressure decreases, and a gaseous phase is formed. This step is controlled both by the nozzle in the device and by adiabatic dry ice formation. Dry ice formation around the nuclei or particles of the substance controls particle growth and prevents aggregation of the nuclei or particles. According to a preferable embodiment ultrasonic agitation of the first nozzle is also performed. This further prevents aggregation of the nuclei or particles and controls the particle growth.

The particle size of organic substances obtained by the method of the present invention is 200 nm or less, preferably less than 100 nm, and more preferably less than 50 nm, and most preferably less than 20 nm.

As defined herein a “nanoparticle” is a particle whose average diameter is 200 nm or less.

As defined herein an “organic substance” is a molecule containing carbon, excluding carbon containing alloys, and relatively small number of carbon-containing compounds such as metal carbonates and carbonyls, simple oxides of carbon and cyanides, as well as allotropes of carbon and simple carbon halides and sulfides which are considered inorganic. Exemplary organic substrates used in the present technology are biologically active materials including medicaments and their pharmaceutically acceptable organic and inorganic salts.

A non-limiting list of exemplary classes of biologically active materials that may be of interest to the technology include analgesics, antagonists, anti-inflammatory agents, anthelmintics, antianginal agents, antiarrhythmic agents, antibiotics (including penicillins), anticholesterols, anticoagulants, anticonvulsants, antidepressants, antidiabetic agents, antiepileptics, antigonadotropins, antihistamines, antihypertensive agents, antimuscarinic agents, antimycobacterial agents, antineoplastic agents, antipsychotic agents, immunosuppressants, antithyroid agents, antiviral agents, antifungal agents, anxiolytic sedatives (hypnotics and neuroleptics), astringents, beta-adrenoceptor blocking agents, blood products and substitutes, anti-cancer agents, cardiacinotropic agents, contrast media, corticosterioids, cough suppressants (expectorants and mucolytics), diuretics, dopaminergics (antiparkinsonian agents), haemostatics, immunosuppressive and immunoactive agents, lipid regulating agents, muscle relaxants, parasympathomimetics, parathyroid calcitonin and biphosphonates, prostaglandins, radiopharmaceuticals, sex hormones (including steroids), antiallergic agents, stimulants and anorexics, sympathomimetics, thyroid agents, vasidilators, neuron blocking agents, anticholinergic and cholinomimetic agents, antimuscarinic and muscarinic agents, vitamins, and xanthines.

The organic substance, such as biologically active materials, such as medicaments, may be crystallic, amorphic or their mixtures. According to one embodiment, the nanoparticles comprise a biologically active agent and one or more excipients.

Exemplary medicaments suitable for the method of the present technology are entacapone, esomeprazole, atorvastatin, rabeprazole, piroxicam and olanzapine. An exemplary medicament is piroxicam (4-hydroxy-2-methyl-N-(2-pyridinyl)-2H-1,2-benzothiazine-3-carboxamide 1,1-dioxide).

The supercritical fluid is preferably $CO_2$, but also other supercritical fluids or their mixtures can be used. The organic substances to be nanosized are dispersed or dissolved in a proper medium, preferably into a supercritical fluid or a near critical fluid. The medium employed in the disclosed process can generally be any of a number of liquefied compressed gases and their mixtures known to the art. These include but are not limited to gaseous oxides such as nitrous oxide; water; alkanes such as ethane, propane, butane, and pentane; alkenes such as ethylene and propylene; alcohols such as ethanol and isopropanol; ketones such as acetone; ethers such as dimethyl or diethyl ether; esters such as ethyl acetate; halogenated compounds including sulfur hexafluoride, chlorofluorocarbons such as trichlorofluoromethane, dichlorofluoromethane, difluorochloromethane, and fluorocarbons such as trifluoromethane; and elemental liquefied gases such as xenon. Optionally, the medium can include mixtures of one or more suitable materials. In general, the biocompatibility of the medium is not an issue in the disclosed process, as the supercritical medium will generally be separated completely after expansion, with the gas leaving the system or being collected for recycling.

According to a particular embodiment, the supercritical fluid is supercritical water. Water is most commonly used solvent and compared to $CO_2$ also more affordable. Using water as a solvent makes the process more applicable and potentially increases the amount of solutes that can be used in the CESS process. Water is even more environmentally friendly than $CO_2$ and due to the lower price of water, the collection and filtration step needed for re-use of the solvent, can be left out of the process.

It is to be understood that also near-supercritical form media can be used. The medium, advantageously a supercritical fluid, can act as a solvent or as an antisolvent.

Figure 4:
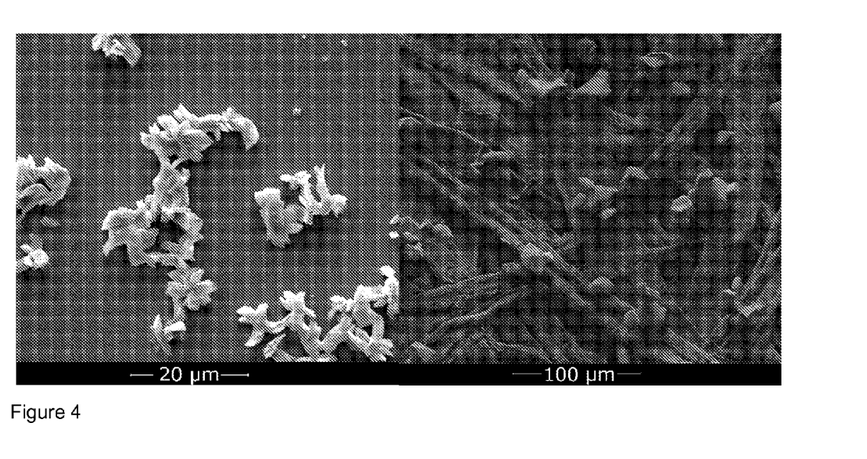
FIG. 4 shows piroxicam particles prepared according to a method of prior art (left: particle size 5 µm; right: particle size 12 µm)
Figure 5:
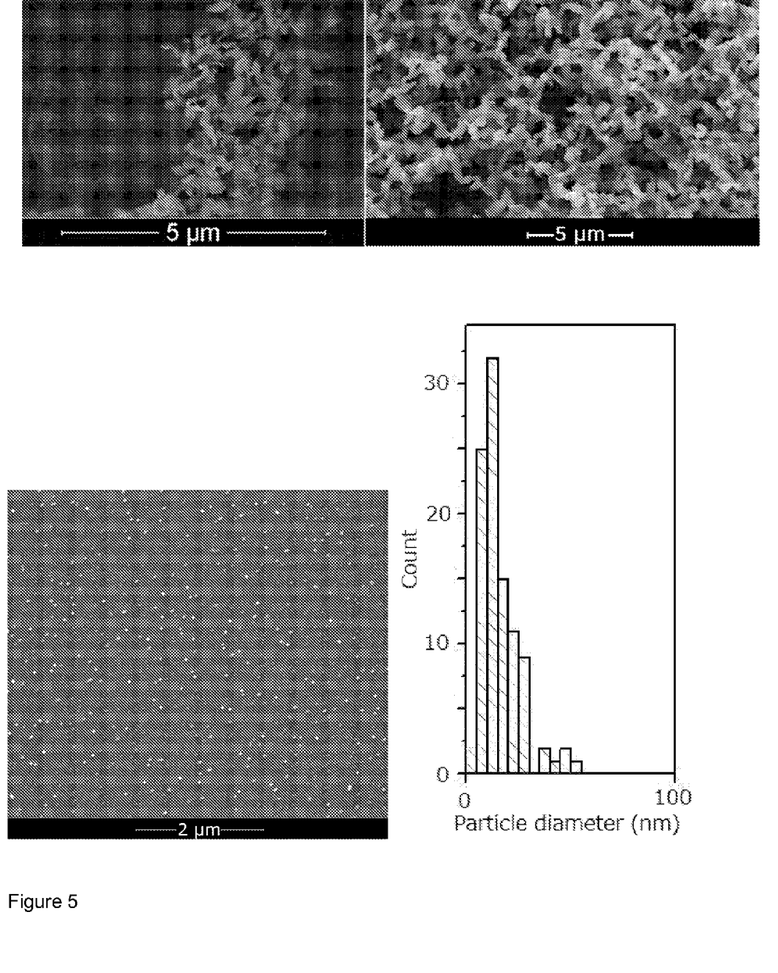
FIG. 5 shows exemplary piroxicam particles prepared according to a method of the present invention (top left: particle size 50 nm; top right: particle size 200 nm; bottom left: particle size 16 nm), bottom right: particle size distribution of the 16 nm particles shown in bottom left.
Figure 6:
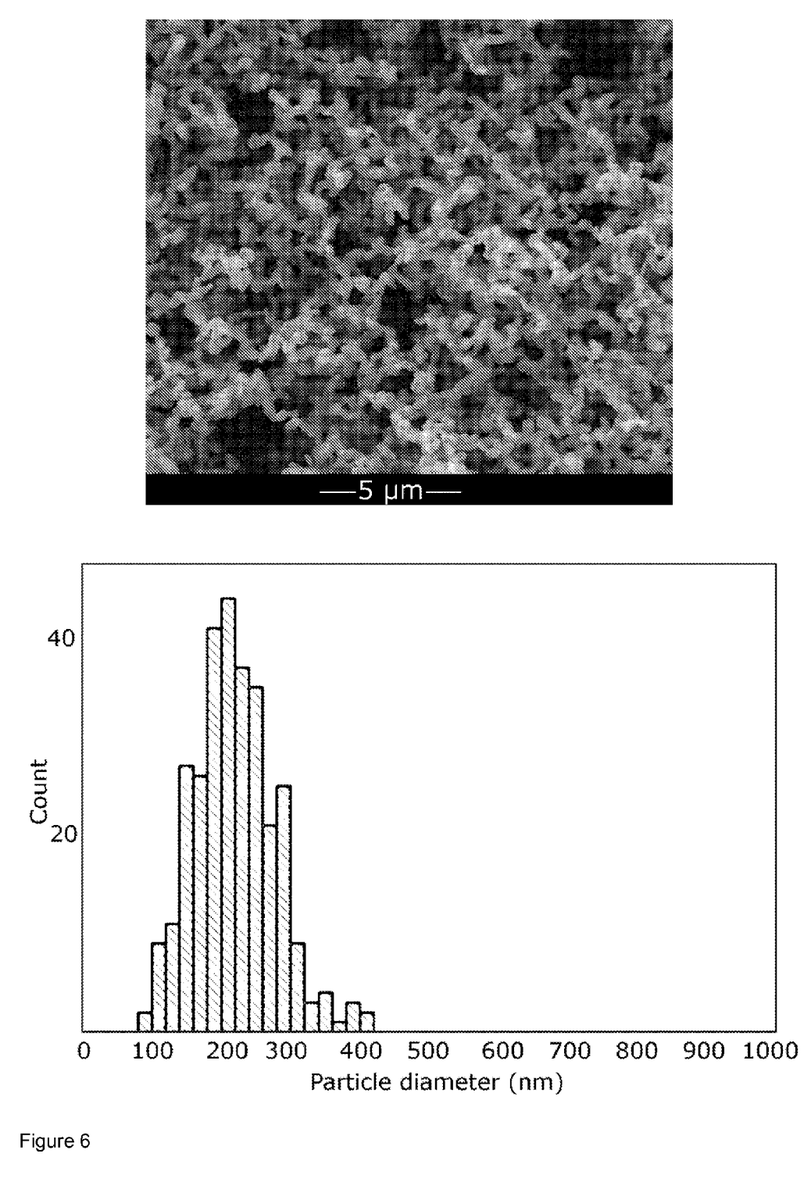
FIG. 6 shows exemplary piroxicam particles and their particle size distribution prepared according to a method of the present invention.
Figure 7:
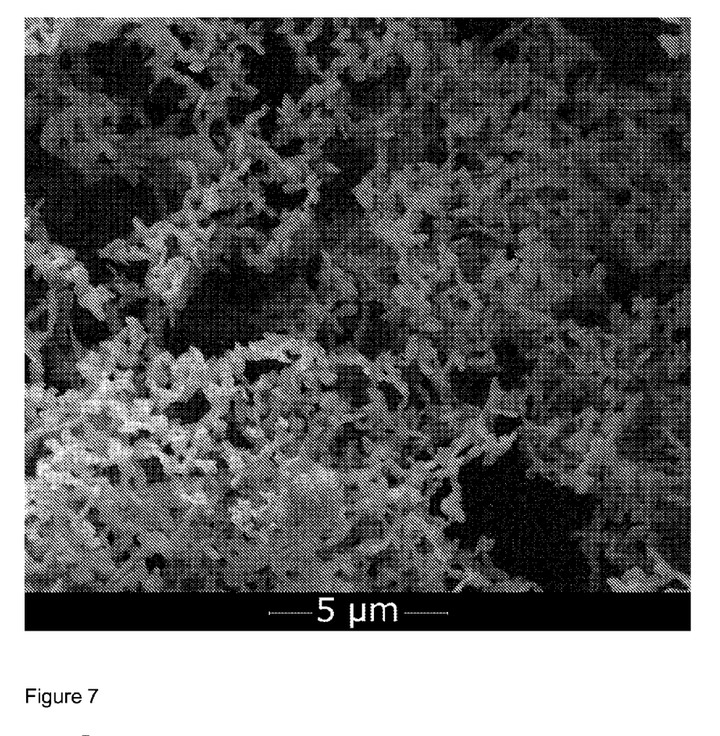
FIG. 7 shows exemplary piroxicam nanoparticles prepared according to an apparatus of the present invention.

FIG. 4 shows particles of a medicament (piroxicam) prepared according to a prior art method, and FIGS. 5-7 show exemplary particles of the same drug prepared according to the present invention. As seen in the figures, a significant reduction in particle size can be achieved by the present method. Particles with narrower size distribution can be produced with more controlled mass transfer in the system.

Figure 8:
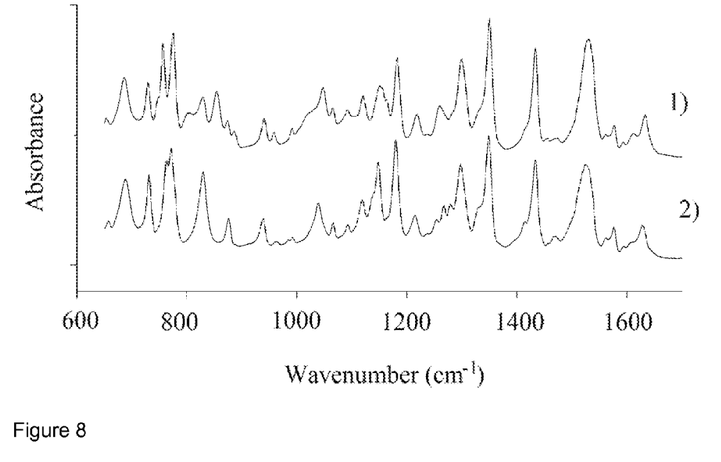
FIG. 8 shows FTIR spectra of bulk piroxicam (top) and piroxicam nanoparticle prepared according the method of the present invention (bottom)

It was surprisingly found that the method of the present invention can be used for polymorphic change of medicaments. According to a particular embodiment, the method was used to convert bulk piroxicam particles of Form I to Form III nanoparticles as judged by FTIR and by comparing with literature data (Vrecer et al. International Journal of Pharmaceutics 256 (2003) pp 3-15). FTIR spectra are shown in FIG. 8.

In an exemplary process using the device in FIG. 2 for producing nanoparticles of piroxicam, formation of dry ice, including the nuclei of piroxicam, started ca 2-3 cm from the first nozzle. The average particle size in this case was 200 nm. According to a preferable embodiment, solidifying $CO_2$ containing particles of the sample substance is subjected to another flow of $CO_2$. The additional flow stops or at least reduces the growth of the particles. Also the collection of the sample substance is simplified.

Accordingly, it is preferable to further enhance the solidification of the fluid, such as dry ice formation, by an additional flow of one or more second fluids in the proximity of the first nozzle (4). This can be achieved by one or more additional nozzles, i.e. second nozzles (6) equipped with a fluid inlet. The distance and the angle of the second nozzles are preferably chosen such that the formation of the solidifying fluid such as dry ice from these nozzles takes place earlier than the formation of the solidifying fluid, such as dry ice, expanding through the first nozzle. The second nozzle can be concentric with the first one. The additional solidifying fluid such as dry ice prevents the increase in particle size of the sample substance. Furthermore, since the formed solid dispersion includes a significant amount of solid fluid, such as dry ice, aggregation of the particles of the sample substance is less prominent. Although $CO_2$ is a preferable second fluid, also other fluids and their mixtures can be used.

According to one embodiment the method includes collection of the nanoparticles, e.g. on a filter (11) located in the collection chamber.

According to another embodiment the method further includes flushing the collection chamber (5), preferably the filter (11) including nanoparticles of the sample substance with dry nitrogen from a second container (12) via a third nozzle (7). Inert nitrogen prevents particle aggregation as the solidified fluid such as dry ice sublimates. It also prevents moisturizing of the particles of the sample substance. Also other inert gases, such as argon can be used for this purpose. The particles remain separate and can be used in drug formulations or stored as a solid dispersion e.g. in dry ice or in liquid nitrogen.

According to another embodiment, the method is used to optimize the solid state form of the substance and to produce advantageous polymorphic forms, crystals mixed with excipients, co-crystals, or amorphous state of the substance. According to one embodiment the method is intended for manufacture of pharmaceutical excipients, active drug substances and drug/drug, drug/excipient and excipient/excipient mixtures. According to one embodiment the excipients are selected from antiadherents, binders, coatings, disintegrants, fillers, flavors, colors, lubricants, glidants, sorbents, preservatives, sweeteners, tracers and ultrasonic or photo acoustic enhancers.

According to one embodiment the present technology is used to produce multi-functional nano-sized colloidal particles (MF colloidal particles), where different components are included in each particle and/or where a significant fraction of particles contains various components in equal ratios. The MF colloidal particles may be partly or totally crystalline and/or amorphous. According to an embodiment the MF particles contain one or more active components, and one or more supportive components that serve to improve machineability, solubility, wetting, dissolution rate, uptake, chemical and/or physical stability, as well as various powder properties, e.g. flowability and biological activity.

According to another embodiment the method is used to produce multifunctional particles including the active substance and various excipients.

According to another embodiment the present invention concerns a device for producing nanoparticles of a substance, the device including:
- a pressure chamber (1) for a mixture of the organic substance and a supercritical fluid,
- a collection chamber (5) for the nanoparticles of the substance,
- an outlet tube (2) connecting the pressure chamber to a collection chamber (5), the outlet tube being provided with
- one or more pressure controlling means (3) configured to control pressure of the mixture within the outlet tube, and
- a first nozzle (4) configured to allow expansion of the mixture to the collection chamber, and
- one or more second nozzles (6), for one or more second fluids, the one or more second nozzles being configured to allow adiabatic solidification of the one or more second fluids, and to allow subjecting the mixture expanding from the first nozzle to the solidifying one or more second fluid.

The outlet tube of the device may include one or more pressure controlling means. The properties of the one or more pressure controlling means such as a needle valve are preferably such that the flow and mass transfer to the outlet tube with certain diameter can be adjusted to achieve desired pressure drop and flow velocity. The nozzle is used to maintain the desired pressure and flow in the outlet tube and the diameter may be selected according to the diameter of the outlet tube and properties of the pressure controlling means. Combination of the valve, the outlet tubing, and the nozzle described enable CESS process by creating correct pressure profile. Exemplary combinations are the following: ≥1/16-1/4 valve opening, outlet tube length 40-60 cm, outlet tube outer diameter 1/8", 0.028 inch wall, nozzle diameter 0.1-0.3 mm.

The first nozzle of the device according to the present invention may be constructed from a material generally used as nozzle materials. Exemplary common materials are various grades of stainless steel. Other exemplary materials are titanium, sapphire, fused quartz, graphene, carbon nanotubes, silicone single crystals, diamonds and their assemblies. The diameter, shape and aspect ratio of the nozzle can be chosen according to the desired flow. According to one embodiment the nozzle includes adjusting means to alter the aspect ratio and/or to modify the geometry of the one or more nozzle channels.

According to one embodiment device includes a nozzle actuation means configured to actuate the first nozzle by focused or unfocussed laser light or high frequency ultrasound. The actuation avoids clogging of the nozzle by the substance. According to a preferable embodiment, the first nozzle is connected to a piezo actuator configured to actuate the exit surface or the external proximity of the first nozzle at a frequency of 1 MHz or higher. The nozzle actuation means is not shown in FIG. 2.

The first nozzle (4) can be any expansion nozzle as is generally known in the art. For example, the nozzle can be a specifically designed and constructed orifice. In one embodiment, the first nozzle is a fused-silica capillary held within stainless steel tubing. According to a preferable embodiment, the first nozzle has an internal diameter between 1 and 100 μm and an aspect ratio (L/D) of at least 5.

The device according to the present invention includes one or more second nozzles for one or more second fluids. The one or more second nozzles (7) are constructed from a material generally used as nozzle materials. An exemplary second nozzle is a ruby nozzle including a 300 μm orifice. According to a preferable embodiment the one or more second nozzles are produced by 3D printing. The advantage of the 3D printing is that the structure of the nozzle can be designed according to the construction of the device and the demands of the organic substance.

The disclosed process can generally utilize any liquefied compressed gases known to the art. These include but are not limited to gaseous oxides such as nitrous oxide; alkanes such as ethane, propane, butane, and pentane; alkenes such as ethylene and propylene; alcohols such as ethanol and isopropanol; ketones such as acetone; ethers such as dimethyl or diethyl ether; esters such as ethyl acetate; halogenated compounds including sulfur hexafluoride, chlorofluorocarbons such as trichlorofluoromethane, and fluorocarbons such as trifluoromethane and elemental liquefied gases such as xenon. Optionally, the process can include mixtures of one or more materials. In general, biocompatibility is not an issue in the disclosed process, as the supercritical fluid will generally completely evaporate and leave the system or be collected for recycling.

According to a preferable embodiment the device according to the present invention further includes a third nozzle (8) configured to fluid the collection chamber with an inert gas. The technical effect of the third nozzle is disclosed above.

Comparison of CESS and RESS Techniques

Table 2 summarizes the differences between RESS and the method according to the present invention (CESS).

TABLE 2

Essential differences between RESS and CESS techniques.

| | RESS | present invention (CESS) |
|---|---|---|
| Pressure drop | rapid | controlled |
| Approximate ratio of pressure drop | >10 | <15; preferably <10 |
| flow velocities in the collection chamber | supersonic | subsonic |
| supersaturation degree | high | low |
| formation of Mach disk | yes | no |
| particle formation | mainly beyond exit nozzle | mainly prior to exit nozzle |
| Main mechanism for particle growth | coagulation | condensation |

In the RESS process, pressure drops with one step from the pre-expansion pressure to the post-expansion pressure, whereas with the method of the present invention (CESS), there is an intermediate pressure reduction i.e. the gradual decrease of pressure (from the first pressure to the second pressure) between the pre-expansion pressure (first pressure) and the post-expansion pressure (third pressure). Accordingly, in the CESS process the pressure is reduced intentionally prior to the first nozzle. This pressure reduction is preferably recorded and monitored with pressure meters.

Figure 9:
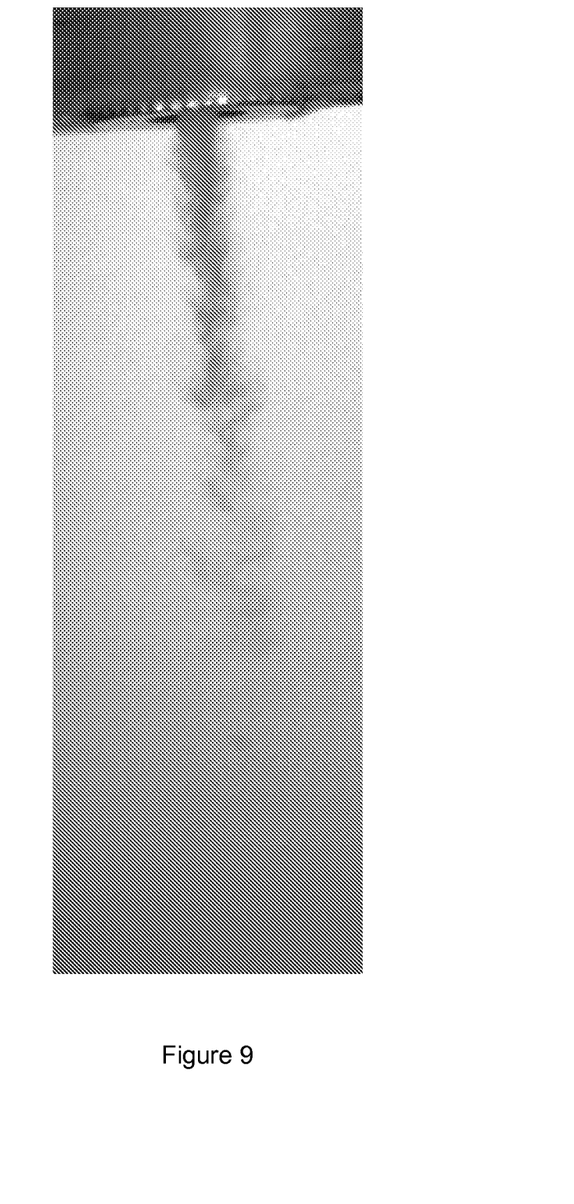
FIG. 9 shows a typical flow of the mixture to the collection chamber (decrease of the second pressure to the third pressure) in a method of the present invention recorded with high-speed camera and FIG. 10 shows exemplary dissolution profiles piroxicam particles prepared according to a method of the present invention and according to a method or prior art.

Ratio of the pressure drop determines the flow velocities, and when flow velocities are supersonic, Mach disks are formed. For the Mach disk formation, the ratio of pressure reduction must usually be more than ten. In strict contrast to RESS, there is no Mach disc formation in the method of the present invention. A typical flow of the mixture from the first nozzle to the collection chamber (decrease of the second pressure to the third pressure) in a method of the present invention recorded with high-speed camera, is shown in FIG. 9. As shown in the figure, no Mach disc formation can be observed.

According to a preferable embodiment, the ratio of pressure drop from first pressure to the second pressure is less than then, and the second pressure to the third pressure is less than ten. The flow velocities in the system is preferably subsonic.

Supersaturation degree (S) is defined by the following equation:

$$S = \frac{y_{2,E}(T_E, p_E) \cdot \Phi_2(y_{2,E}, T_E, p_E)}{y_{*2}(T, p) \cdot \Phi_2(y_{*2}, T, p)}$$

wherein $T_E, p_E$ is the pre-expansion temperature and pressure, $T, p$ is the post-expansion temperature and pressure, $y_{Z,E}$ is the mole fraction at the pre-expansion state, $y_{*2}$ is the equilibrium mole fraction of the solute at the post-expansion state, and $\phi_2$ is the solute fugacity coefficient (fugacity coefficient relates the ideal gas pressure and the effective pressure a real gas replacing the true mechanical pressure). Accordingly, the higher is the ratio between pre- and post-expansion conditions, the higher the supersaturation degree. The higher is the supersaturation degree, the more and the smaller nuclei are formed. In the RESS process it is unorthodox for the pressure to drop within the capillaries of the nozzle. When describing and modeling the RESS process in the literature, pressure drop in the nozzle is usually considered causing lower supersaturation levels and leading to formation of larger particles. These investigations and models are restricted to nozzle capillaries shorter than 20 mm. These nozzle capillaries that allow even this very small pressure reduction are prone to clog the system and thus there are no results with longer nozzles. Significant pressure reduction earlier in the process (e.g. prior to the nozzle) is non-compatible with the principles of the RESS process. This kind of pressure profile is considered to lead to clogging and not considered even a possibility in RESS process. The main principle of RESS is to create as high supersaturation level as possible and thus the aim for the nucleation and particle formation to take place in the collection chamber.

In contrast the present invention is aimed to reproducibly prepare nanosized particles with the pressure profile that is considered impossible in the RESS process. In the CESS process low supersaturation levels are acceptable and particle formation takes more time and due to the laminar or near-laminar flow the formed particles are transported smoothly to the exit nozzle that in the CESS process functions as a flow controller rather than an expansion device as described earlier.

In the CESS process there is no relevant phase change of the solute at the nozzle, since the supersaturation occurs in the outlet tube. In the CESS process separate heating unit is not needed at the nozzle. The flow velocities or the pressure drop at this point is not adequate for causing the freezing the nozzle.

Condensation is particle growth caused by the deposition of the free molecules on the surface of the formed nuclei. In RESS process the time available for particle growth by condensation is limited to microseconds. In CESS process condensation is the main mechanism for particle growth taking place the outlet tube, i.e. when the first pressure is decreased gradually to the second pressure. The condensation step in the system may be optimized by the volume of the outlet tube and the diameter of the nozzle.

In the RESS process the main mechanism for particle growth is coagulation in the subsonic free jet. Particles are mainly formed in the collection chamber and the particle concentration is highest at the Mach disk. Particle growth is accelerated beyond the shock in the expansion jet causing uncontrollable particle growth. In the CESS process the coagulation step is reduced at the expense of allowing the particle size to grow by condensation within the outlet tube. In the CESS process coagulation is further prevented by the formation of dry ice that creates a solid dispersion consisting of nanoparticles and dry ice.

RESS devices/technique aim(s) to rapidly decrease the pressure, thus the devices aim to maintain the pressure at the pressure chamber level until the exit nozzle. If the pressure reduces prior to the expansion chamber, pressure reduction takes place in the capillary of the exit nozzle (i.e. in a μm-mm range capillary) and happens in microseconds. This pressure reduction does not provide stable pressure region/step-wise pressure reduction such as in the outlet tube of the device according to the present invention. Devices used for RESS are not built to create conditions of the pressure profile needed for CESS.

Particle formation with RESS process takes mainly place in the collection chamber. The pressure is reduced immediately to ambient pressure. According to RESS, no back pressure is employed, and flow velocities are supersonic, Mach disk is formed, supersaturation levels are high and formed nuclei are small and the particles grow mainly by coagulation. In strict contrast to the method of the present invention, large nuclei are considered as disadvantage with RESS process and thus low supersaturation levels are avoided.

EXPERIMENTAL

Piroxicam (Hawkings Inc., U.S.) and $CO_2$ (purity ≥99.8% AGA, Finland) were used for particle production. Phosphate buffer (100 mM; pH 7.2) used in the dissolution tests was prepared according to the European Pharmacopoeia (Ph. Eur. 7th ed.). All the reagents were used as received and were of analytical grade.

Comparative Example

Traditional RESS devices were tested with piroxicam for reference. Both a laboratory scale device and a pilot scale RESS device was employed. In the laboratory scale device, a 200 bar pressure and 60° C. temperature in the pressure chamber as well as a RESS orifice with diameter 100 μm were used. No collection chamber was used. In the pilot scale device particles were produced at 200-230 bar and 60° C. with a collection chamber at 55 bar and 31° C.

The average particle size of particles prepared with the laboratory scale device and with the pilot scale device were 5 μm and 12 μm, respectively. Examples of the particles are shown in FIG. 4.

Example 1

The system's main components were a high pressure pump (SFT-10, Supercritical Fluid Technologies, Inc., USA), a custom high pressure chamber, a heater/mixer (MR 2002, Heidolph, Germany), a ruby nozzle (150 μm orifice) and a collection chamber. The pressure chamber was loaded with a sample substance (piroxicam; 300 mg, saturated) followed by liquid $CO_2$. Pressure and temperature was increased to 200-310 bar and 60° C., respectively. A magnetic mixer (1500 rpm) ensured proper dissolution of the sample substance and formation of a homogenous mixture. Supersaturation state was obtained within 30 min.

The first pressure reduction step was allowed to take place in the needle valve of the outlet tube connecting the pressure chamber to the collection chamber. The sample substance was allowed to release into the collection chamber through a nozzle. The flow rate inside the outlet tube (length 60 cm, diameter 2 mm) was kept at 24 mL/min with the aid of a needle valve (SS-3HNTF2, Swagelok) to ensure laminar flow. Accordingly, the pressure was allowed to decrease gradually to a non-supercritical state to initiate the nucleation of the sample substance within the outlet tube.

The second pressure reduction step was allowed to take place at the exit nozzle (i.e. the first nozzle), As the $CO_2$ volume was increased, a gaseous $CO_2$ phase was formed. This step was controlled by adiabatic dry ice formation. Dry ice formation around the nuclei controlled particle growth and prevented aggregation of the nuclei.

Dry nitrogen was used to flush the collection chamber. Inert $N_2$ prevented particle aggregation as dry ice sublimates. The particles remained separate. The particles were stored as a solid dispersion and dry ice. Finally, they were collected as dry powder of pure nanoparticles after sublimation of $CO_2$. The chemical integrity and polymorphism of the nanoparticles were evaluated with Fourier transformed infrared spectroscopy (FTIR). FTIR spectra were recorded at room temperature using a Vertex 70 (Bruker, USA) with a horizontal attenuated total reflectance (ATR) accessory (MIRacle, PIKE Technologies, USA) between 4000-650 $cm^{-1}$. This provided a 4 $cm^{-1}$ resolution when using the OPUS 5.5 software.

50 nm particles were collected with a preparation process of 150-250 bar and 70° C. in the pressure chamber using a flattened tube nozzle. Examples of particles are shown in FIG. 5 (top left).

200 nm particles were prepared reproducibly with a steady process with 150-330 bar and 60-90° C. in the pressure chamber featuring a Ø=150 μm ruby nozzle. With both processes the flow in the outlet tube from the pressure chamber to the nozzle was controlled and kept near laminar. A needle valve was used to control the flow and after the adiabatic dry ice formation at the nozzle was established. Examples of particles are shown in FIG. 5 (top right)

16 nm particles were formed in conditions where the $CO_2$ flow from the outlet tube was kept very slow and the pressure chamber was used at 200 bar and 60° C. A needle valve was used to control the flow and the particles were collected on glass slides. Examples of particles are shown in FIG. 5 (bottom).

Example 2. The Effect of Second Fluid a) Piroxicam in $scCO_2$ was allowed to expand through the first nozzle to the collection chamber at 330 bar and 72° C. The particle size was 500 nm.
b) Piroxicam in $scCO_2$ was allowed to expand through the first nozzle to the collection chamber at 330 bar and 72° C., and additional $CO_2$ through the second nozzle was subjected to the forming particles of piroxicam. Particle size obtained was 200 nm. Examples of particles are shown in FIG. 7.

Determination of Particle Size

Particle size and morphology of the particles were examined by scanning electron microscopy (SEM). Piroxicam nanoparticles and bulk (reference) piroxicam were imaged with a Quanta™ 250 FEG (FEI Inc., U.S.). Samples were collected on a metal net residing on a carbon-coated double-sided tape. Samples were sputter-coated with a 5 nm thin layer of platinum (Q150T Quomm, Turbo-Pumped Sputter Coater, China). The coated samples were imaged in 9.85× $10^{-4}$ Pa pressure, with 30 μm aperture, 10 kV, ≤200 nA, and a 2.5 nm spot size. Each image was obtained in ca 5 minutes. The particle size was determined by diameter measurements and analysis with the ImageJ freeware (National Institutes of Health, USA).

The average diameter of the nanoparticles prepared as disclosed in Example 1 was 210 nm±59 nm (n=300). The size distribution of the nanoparticles was narrow (FIG. 6) and the formed particles were round with a slightly elongated shape and with no visible fracture planes or aggregates (FIG. 7). The smallest particles obtained according to the method were 16 nm.

Drug Release Tests

Drug release tests for piroxicam nanoparticles and bulk (reference) piroxicam were done to investigate the effect of particle size on the dissolution rate. The tests were conducted in glass vials under heating (37.0±0.5° C.) and stirring (400 rpm) (H+P Labortechnik AG, Multitherm, Germany). Samples were placed in a gelatin capsule and anchored with an iron wire to prevent the capsule from surfacing.

The capsule was then placed in glass vials containing phosphate buffer (50 mL; pH 7.2). Aliquots (1 mL) were taken at the time points ranging from 1 min to 48 hours. Drug release tests were conducted in triplicate. Samples were analyzed with high performance liquid chromatography (HPLC Thermo System Products, Agilent 1200 Infinity Series, Agilent Technologies, Germany) using a Discovery® C18 (Supelco Analytical, U.S.) column with guard column and a flow rate of 1 mL/min. The mobile phase was 60:40 (v/v) acetonitrile and 0.05% trifluoroacetic acid. The UV detection of piroxicam was set to 333 nm with a retention time of 2.9 min and total run time of 4 min at 30° C. A standard curve for BSA quantification was made from piroxicam concentrations of 0.1-25 μg/mL ($R^2$=0.999).

Figure 10:
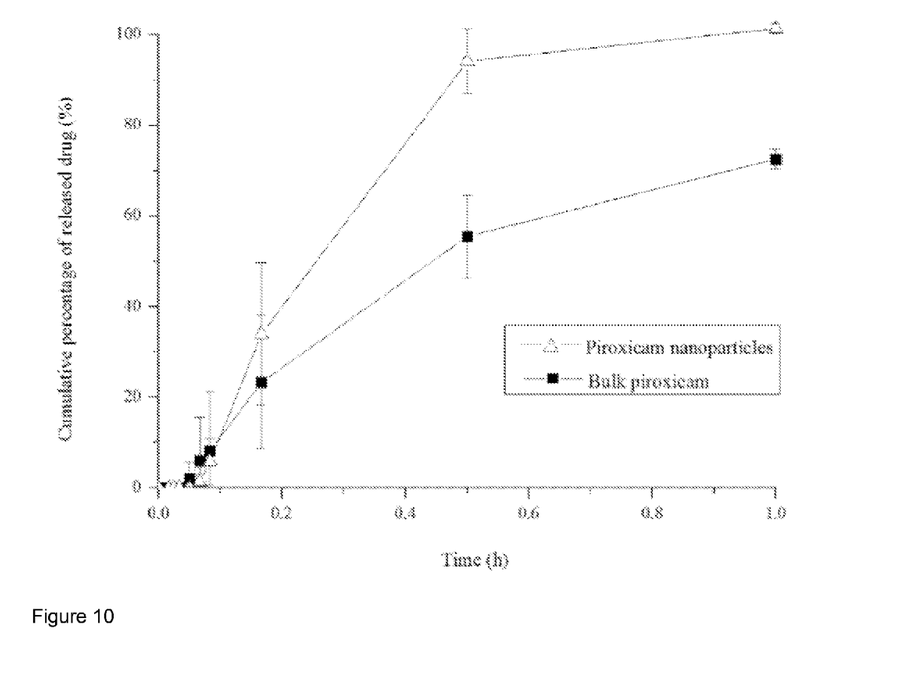

FIG. 10 illustrates the dissolution profiles of the nanoparticles and bulk piroxicam. The dissolution rate of the bulk piroxicam agreed and exceeded that reported in the literature [Lai et al. 2011 doi: 10.1016/WEJPB.2011.07.005]. The dissolution rate of the nanoparticles was twice that of the dissolution rate of bulk piroxicam. The gelatin capsules caused a lag time of 1-2 min in the dissolution rate profiles. All samples completely dissolved within 24 hours. Nanoparticles were completely dissolved from the gelatin capsules within one hour from the beginning of the test.

The non-limiting, specific examples provided in the description given above should not be construed as limiting the scope and/or the applicability of the appended claims.

The invention claimed is:
1. A method for producing nanoparticles of an organic substance, the method comprising;
admixing the organic substance and a supercritical fluid to form a mixture at a first pressure,
decreasing the first pressure gradually to a second pressure so that a flow of the mixture is formed and nucleation of the organic substance in the mixture is initiated, and decreasing the second pressure to a third pressure, so that solidification of the fluid of the mixture, including the nucleated organic substance, is initiated, wherein ratio of pressure drop from the first pressure to the second pressure is less than 15, and wherein ratio of pressure drop from the second pressure to the third pressure is less than 15.

2. The method according to claim 1, wherein the solidification is adiabatic.

3. The method according to claim 1, wherein the flow is substantially laminar.

4. The method according to claim 3, wherein the flow is partially turbulent.

5. The method according to claim 1, wherein the second pressure is less than 100 bar.

6. The method according to claim 1, wherein decreasing the second pressure to the third pressure is carried out by expanding the mixture from the second pressure to the third pressure through a first nozzle.

7. The method according to claim 6 further comprising actuating the first nozzle.

8. The method according to claim 7, wherein the actuating is caused by an ultrasound operated at a frequency of at least 20 kHz.

9. The method according to any of claim 1 further comprising;

obtaining one or more second fluids, allowing the one or more second fluids to expand so adiabatic solidification of the one or more second fluids is initiated, and subjecting the mixture including the nucleated organic substance to the solidifying one or more second fluid.

10. The method according to claim 1, wherein the supercritical fluid comprises carbon dioxide.

11. The method according to claim 9, wherein the one or more second fluids includes carbon dioxide.

12. The method according to claim 1, further comprising collection of the nanoparticles.

13. The method according to claim 1, further comprising flushing the nanoparticles with an inert gas.

* * * * *